United States Patent
Rittig et al.

(10) Patent No.: US 9,822,187 B2
(45) Date of Patent: Nov. 21, 2017

(54) METHOD FOR PROCESSING CELLULOSE-CONTAINING BIOMASS

(71) Applicant: BASF SE, Ludwigshafen (DE)

(72) Inventors: Frank Rittig, Worms (DE); Michael Koch, Speyer (DE); Vaidotas Navickas, Mannheim (DE); Stefan Koch, Mainz (DE); Alois Kindler, Gruenstadt (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/024,387

(22) PCT Filed: Oct. 2, 2014

(86) PCT No.: PCT/EP2014/071181
§ 371 (c)(1),
(2) Date: Mar. 24, 2016

(87) PCT Pub. No.: WO2015/049345
PCT Pub. Date: Apr. 9, 2015

(65) Prior Publication Data
US 2016/0237170 A1     Aug. 18, 2016

(30) Foreign Application Priority Data

Oct. 2, 2013 (EP) .................... 13187189

(51) Int. Cl.
| | |
|---|---|
| C08B 1/00 | (2006.01) |
| C08H 8/00 | (2010.01) |
| C12P 7/10 | (2006.01) |
| C12P 19/02 | (2006.01) |
| C12P 19/14 | (2006.01) |
| C12P 7/16 | (2006.01) |
| C12P 7/46 | (2006.01) |

(52) U.S. Cl.
CPC ............ *C08B 1/00* (2013.01); *C08H 8/00* (2013.01); *C12P 7/10* (2013.01); *C12P 7/16* (2013.01); *C12P 7/46* (2013.01); *C12P 19/02* (2013.01); *C12P 19/14* (2013.01); *C12P 2201/00* (2013.01); *Y02E 50/10* (2013.01); *Y02E 50/16* (2013.01)

(58) Field of Classification Search
CPC ....................................................... C08B 1/00
See application file for complete search history.

(56) References Cited

U.S. PATENT DOCUMENTS

| | | | |
|---|---|---|---|
| 8,524,924 B2 * | 9/2013 | Burket ................. | C07D 307/50 549/488 |
| 2004/0231060 A1 | 11/2004 | Burdette et al. | |
| 2005/0191736 A1 | 9/2005 | Brown et al. | |
| 2011/0262984 A1 | 10/2011 | Nguyen | |

FOREIGN PATENT DOCUMENTS

| | | |
|---|---|---|
| EP | 2 033 974 A1 | 3/2009 |
| WO | WO-2008/134037 A1 | 11/2008 |
| WO | WO-2012/103220 A1 | 8/2012 |

OTHER PUBLICATIONS

Technical data sheet, 2011.*
qing, impact of surfactants of pretreatment of corn stover, 2010, Bioresource Technology, pp. 5941-5951.*
International Search Report for International Patent Application No. PCT/EP2014/071118, dated Jan. 23, 2015.

* cited by examiner

*Primary Examiner* — Melvin C Mayes
*Assistant Examiner* — Stefanie Cohen
(74) *Attorney, Agent, or Firm* — Marshall, Gerstein & Borun LLP

(57) ABSTRACT

Described are a method for processing cellulose-containing biomass and the use of methanesulfonic acid for processing cellulose-containing biomass, especially for the pretreatment of cellulose-containing biomass prior to saccharification.

16 Claims, No Drawings

METHOD FOR PROCESSING CELLULOSE-CONTAINING BIOMASS

CROSS-REFERENCE TO RELATED APPLICATIONS

This is the U.S. national phase of International Application No. PCT/EP2014/071181, filed Oct. 2, 2014, which claims the benefit of European Patent Application No. 13187189.9, filed Oct. 2, 2013.

Sugars generated from cellulose-containing biomass may be used as a feedstock for production of fuels, plastics, and other chemicals. Due to the finite nature and instability of fossil feedstock supply and for environmental reasons, replacement of fossil feedstock by non-fossil feedstock, i.e. feedstock obtained from renewable resources, becomes more and more important. One potential source of such non-fossil feedstock is cellulose-containing biomass, which can be processed by enzymatic saccharification of cellulose to glucose which can be further processed into a plurality of products either chemically or by fermentation. For instance, by fermentation of the obtained glucose ethanol (sometimes referred to as bio-ethanol) is obtainable which can be used as fuel for internal combustion engines, e.g. for cars.

In order to facilitate enzymatic saccharification, cellulose-containing biomass is usually subjected to a pretreatment in order to increase the accessibility of the cellulose biomass by degradation or decomposition of the hemicellulose and/or lignin present in the cellulose-containing biomass. Several pretreatment processes are known in the art.

US 2004/0231060 A1 describes a method for hydrolyzing lignocellulose, comprising contacting said lignocellulose with at least one chemical under moderate conditions comprising a temperature from about 10° C. to about 90° C., a pressure less than about 2 atm; and a pH between about 4.0 and about 10.0 to generate a treated lignocellulose, and contacting said treated lignocellulose with at least one enzyme capable of hydrolyzing lignocellulose, wherein said chemical is selected from the group consisting of oxidizing agents, e.g. hydrogen peroxide or nitric acid, denaturants, detergents, organic solvents, bases, and combinations thereof.

US 2005/0191736 A1 describes a method wherein prior to enzymatic saccharification cellulose-containing biomass is heated, either directly with steam or in slurry where a catalyst may also be added to the material to speed up the reactions. Catalysts include strong acids, such as sulfuric acid and $SO_2$, and alkali, such as sodium hydroxide.

US 2011/0262984 A1 discloses a method for pretreatment of cellulosic biomass feedstock comprising cellulose, hemicellulose and lignin, the method comprising spraying an acidic liquid medium onto the cellulosic biomass feedstock to form an acid-impregnated cellulosic biomass feedstock, and agitating said feedstock to distribute said acidic liquid medium within said feedstock and bring particles of the feedstock into mutually abrading contact, and also another method for pretreatment of cellulosic biomass feedstock comprising cellulose, hemicellulose, and lignin, the method comprising: contacting the cellulosic biomass feedstock with an aqueous liquid medium comprising an acid and a surfactant (wetting agent) to form an acid-impregnated biomass feedstock. The acid is typically selected from the group consisting of hydrochloric acid, sulfuric acid, sulfurous acid, sulfur dioxide, nitric acid, and combinations thereof, wherein sulfuric acid solution containing at least about 50 wt.-% sulfuric acid, more preferably at least about 80 wt.-% sulfuric acid, or at least about 90 wt.-% sulfuric acid is preferred.

According to WO 2008/134037, enzymatic digestibility of corn stover is enhanced by a pretreatment including addition of surfactants, e.g. polyoxyethylene sorbitan monolaurate, at 160° C. to 220° C. with and without acid, e.g. sulfuric acid.

According to WO 2012/103220, a feedstock for enzymatic saccharification is prepared by autohydrolysis, which is preferably conducted in a steam explosion reactor also known as a hydrolyzer or as a digester. Said autohydrolysis is a process of breaking down hemicellulose and cellulose by exposure to high temperatures, steam and pressure, sometimes in the presence of an added chemical agent, such as an organic or inorganic acid, e.g., sulfuric acid. During a steam explosion treatment, a cellulosic feedstock is subjected to elevated temperatures, e.g. 180° C. to 220° C. and pressure, e.g., 130 psig to 322 psig, optionally in the presence of suitable chemicals (e.g. organic and/or inorganic acids, ammonia, caustic soda, sulfur dioxide, solvents etc.) in a pressurized vessel.

Typically, in the methods known in the art, the biomass is treated with aggressive chemicals like strong acids (especially sulfuric acid) or oxidizing agents, often in combination with harsh processing conditions like temperatures up to 220° C. For reasons of safety, environment protection and in order to mitigate the requirements to the processing equipment with regard to corrosion stability and heat resistance, it is generally desirable to avoid or at least to reduce the use of aggressive chemicals and harsh processing conditions. Furthermore, aggressive chemicals as well as high temperatures may induce undesirable side reactions beyond the desired degradation of the hemicellulose and/or lignin. According to own experiments, this applies especially for sulfuric acid, which is commonly used in prior art acid treatments of cellulose-containing biomass. Sulfuric acid may act as an oxidation agent and/or as a dehydrating agent, therefore undesired by-products are typically formed by coking and/or sulfatization of biomass constituents. Formation of such by-products in turn results in reduction of the amount of material available for saccharification, contamination of the reaction mixture, deactivation of enzymes used for saccharification, contamination of the reaction equipment (i.e. by formation of insoluble deposits) and difficulties in separating the phases of the treatment mixture.

Accordingly it is an object of the present invention to provide a method for processing cellulose-containing biomass which allows to reduce or even to avoid the use of aggressive chemicals like sulfuric acid without compromising the yield of glucose obtainable by saccharification of the treated cellulose-containing biomass. Preferably, the method to be provided shall result in an increased yield of glucose obtainable by saccharification of the treated cellulose-containing biomass.

In some prior art methods for the processing of cellulose-containing biomass, sulfuric acid is used in combination with surfactants which are considered to have a positive influence on the yield of glucose in saccharification of the treated cellulose-containing biomass. However, the addition of surfactants is not always possible or desirable, due to equipment constraints or due to the high costs of such surfactants. Furthermore, reducing the number of necessary starting materials reduces the complexity of the process and facilitates processing of cellulose-containing biomass in rural regions where large amounts of cellulose-containing biomass are available, but supply of specialized chemicals like surfactants might be difficult.

Accordingly, in a related aspect, it is an object of the present invention to provide a method for processing cellulose-containing biomass in the absence of surfactants and other additives which results in an increased yield of glucose obtainable by saccharification of the treated cellulose-containing biomass.

These and other objects are achieved by the method for processing cellulose-containing biomass according to the present invention. Said method for processing cellulose-containing biomass comprises the step of subjecting a treatment mixture comprising said cellulose-containing biomass, water and methanesulfonic acid to a temperature in the range of from 100° C. to 200° C. at a pressure in the range of from 1 to 20 bars (100 to 2000 kPa) wherein the pressure is selected so that at least a part of the water is in the liquid state to generate a treated cellulose-containing biomass, (i) wherein said treatment mixture further comprises one or more compounds selected from the group consisting of compounds of formula (I)

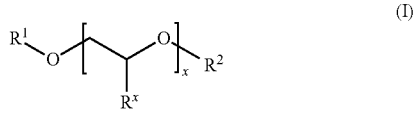

and surfactants which are not compounds of formula (I); wherein in formula (I)

$R^1$ and $R^2$ are independently selected from the group consisting of hydrogen, unsubstituted and substituted alkyl with 1 to 22 carbon atoms ($C_1$- to $C_{22}$-alkyl) and unsubstituted and substituted aryl, wherein in said substituted $C_1$- to $C_{22}$-alkyl and said substituted aryl each substituent is independently selected from the group consisting of —$OSO_3H$, —$SO_3H$, —COOH and —$OPO_3H_2$ and salts thereof each $R^x$ in said $x$ groups

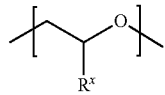

is independently of each further $R^x$ selected from the group consisting of hydrogen and alkyl with 1 to 20 carbon atoms ($C_1$- to $C_{20}$-alkyl)

x is an integer from 1 to 2400 or (ii) wherein said treatment mixture does not comprise any compound selected from the group consisting of compounds of formula (I) as defined above and does not comprise any surfactant which is not a compound of formula (I) as defined above.

Further aspects of the present invention relate to a treated cellulose-containing biomass obtainable by the method according to the invention (as defined hereinabove and described in further detail hereinbelow) and to the use of methanesulfonic acid for processing cellulose-containing biomass, especially for the pretreatment of cellulose-containing biomass prior to saccharification. In this aspect of the present invention, methanesulfonic acid is used either (i) in the presence of one or more compounds selected from the group consisting of compounds of formula (I) and surfactants which are not compounds of formula (I)

or (ii) in the absence of any compound selected from the group consisting of compounds of formula (I) and any surfactant which is not a compound of formula (I).

As far as herein reference is made to methanesulfonic acid as a constituent of the treatment mixture, the term methanesulfonic acid shall be construed to include the protonated as well as the dissociated form of methanesulfonic acid.

The pH value of the treatment mixture is preferably in a range of from 0 to 2, more preferably from 0.5 to 1.5.

Surfactants, i.e. compounds that lower the surface tension of a liquid or the interfacial tension between two liquids or between a liquid and a solid, are generally known. Surfactants are organic compounds that are amphiphilic, meaning that each of their molecules contains one or more hydrophobic regions as well as one or more hydrophilic regions.

The group of compounds of formula (I) consists of compounds which are surfactants and compounds which are not surfactants. Those compounds of formula (I) wherein the molecules each contain a hydrophilic region and a hydrophobic region are surfactants.

Compounds of formula (I) include ionic and non-ionic compounds, and surfactants which are not compounds of formula (I) include ionic and non-ionic surfactants. As far as herein reference is made to an ionic compound of formula (I) or to an ionic surfactant which is not a compound of formula (I) as a constituent of the treatment mixture, said ionic compound of formula (I) as well as said ionic surfactant which is not a compounds of formula (I) shall be construed to include the non-dissociated as well as the dissociated form of said ionic compound of formula (I) or of said ionic surfactant which is not a compound of formula (I), resp., if not specified otherwise. In those cases where an ionic compound of formula (I) or an ionic surfactant which is not a compound of formula (I) is a salt the cation is preferably selected from the group consisting of ammonium, alkali metal cations and alkaline earth metal cations.

In alternative (i) of the method and the use according to the present invention, compounds of formula (I) as defined above (i.e. surfactants of formula (I) as well as compounds of formula (I) which are not surfactants) are more preferred than surfactants which are not compounds of formula (I).

According to alternative (ii) of the method and the use according to the present invention, the treatment mixture is free of compounds of formula (I) (surfactants or not) and also free of surfactants which are not compounds of formula (I).

The step of subjecting a treatment mixture as defined above comprising said cellulose-containing biomass, water and methanesulfonic acid to a temperature in the range of from 100° C. to 200° C. at a pressure in the range of from 1 to 20 bars (100 to 2000 kPa) wherein the pressure is selected so that at least a part of the water is in the liquid state facilitates saccharification, either enzymatic or chemical saccharification, of the obtained treated cellulose-containing biomass. Therefore, in a preferred method according to the present invention, said step provides a useful pretreatment of cellulose-containing biomass for saccharification, either enzymatic or chemical saccharification, or for the production of dissolving pulp.

The treated cellulose-containing biomass typically comprises cellulose, hemicellulose and lignin as major components. In contrast to the cellulose-containing biomass before processing, in the treated cellulose-containing biomass the content of hemicellulose and/or lignin is typically decreased due to decomposition to xylose and other degradation products which may include minor amounts of glucose. Accordingly, in a preferred method of the present invention, the composition of the treatment mixture and the temperature and pressure to which said treatment mixture is subjected are selected such as to decrease the amount of hemicellulose and/or lignin in the cellulose-containing biomass.

Treatment Mixture

The treatment mixture comprises a solid phase comprising cellulose containing biomass and a liquid aqueous phase comprising water, methanesulfonic acid and either (i) one or more compounds selected from the group consisting of compounds of formula (I) and surfactants which are not compounds of formula (I)

or (ii) no compound selected from the group consisting of compounds of formula (I) as defined above and no surfactant which is not a compound of formula (I) as defined above.

Cellulose-containing biomass which is suitable for processing by the method of the present invention may be selected from the group consisting of plant biomass, agricultural wastes, forestry residues, sugar processing residues, paper waste and blends thereof. For economical and ecological reasons, cellulose containing biomass in the form of wastes and residues is especially preferably. Beside cellulose, cellulose-containing biomass typically comprises lignin and/or hemicellulose.

Preferably said treatment mixture comprises 3 wt.-% to 75 wt.-%, more preferably 8 wt.-% to 70 wt.-%, further preferably 15 wt.-% to 60 wt.-%, most preferably 25 wt.-% to 50 wt. %, particularly preferably 30 wt.-% to 45 wt.-% of cellulose containing biomass, in each case based on the total weight of said treatment mixture. With a lower concentration of cellulose-containing biomass in the treatment mixture, the method becomes inefficient, because a very large volume of treatment mixture is handled for obtaining a small amount of treated cellulose-containing biomass. With a higher concentration of biomass in the treatment mixture, there is an issue that not all of the cellulose-containing biomass is in contact with the methanesulfonic acid and—if present—the one or more compounds selected from the group consisting of compounds of formula (I) as defined above (i.e. surfactants of formula (I) as well as compounds of formula (I) which are not surfactants) and surfactants which are not compounds of formula (I).

Beside the cellulose-containing biomass, the treatment mixture comprises at least water and methanesulfonic acid.

Methanesulfonic acid ($CH_3SO_2(OH)$, sometimes abbreviated as MSA) is commercially available e.g. as an aqueous solution comprising 70 wt.-% of methanesulfonic acid (e.g. Lutropur® MSA from BASF) and in anhydrous form (e.g. Lutropur® MSA100 from BASF). Methanesulfonic acid is infinitely soluble in water and has a pKa of −1.9 which is considerably lower than the pKa of the first stage of dissociation sulfuric acid (−3 for the first stage of dissociation, 1.9 for the second stage of dissociation). Methanesulfonic acid has a lower corrosivity in comparison to sulfuric acid, nitric acid, hydrochloric acid, and in contrast to sulfuric acid and nitric acid it does not act as an oxidizing and/or dehydrating agent. Thus formation of undesired by-products, e.g. by coking of the biomass, is avoided and the yield of desired products is increased, and discoloration of the treated biomass is reduced.

Depending on the method of production of the methanesulfonic acid, one or more substances selected from the group consisting of sulfuric acid and salts thereof, hydrochloric acid and salts thereof, organochloro compounds, nitric acid and salts thereof, and metals may be admixed to the methansesulfonic acid.

A further advantage of methanesulfonic acid over sulfuric acid is that methanesulfonic acid is a significantly less strong sulfonation agent than sulfuric acid. Accordingly, emulsions and soap-like products are formed in a lower amount, and phase separation is faster and more efficient.

Moreover, most salts of methanesulfonic acid are easier soluble in water than salts of sulfuric acid, so that problems due to formation of insoluble deposits are reduced.

A further advantage of methanesulfonic acid is its biodegradability both under aerobic and anaerobic conditions.

Preferably, in the treatment mixture the total amount of further acids selected from the group consisting of mineralic acids (sulfuric acid, nitric acid, hydrochloric acid and phosphoric acid) is 100 wt.-% or less, preferably 50 wt.-% or less and more preferably 10 wt.-% or less, based on the weight of the methanesulfonic acid present in the treatment mixture. However, in order to reduce the use of aggressive chemicals, which may cause the above-mention problems regarding safety, corrosion and formation of side products, it is preferred that the treatment mixture does not contain more than 1 wt.-% sulfuric acid, based on the weight of the methanesulfonic acid present in the treatment mixture, and does not contain any other mineralic acid.

In a particularly preferred method according to the invention, the treatment mixture consists of either (i) cellulose-containing biomass, water, methanesulfonic acid, one or more compounds selected from the group consisting of compounds of formula (I) and surfactants which are not compounds of formula (I) and optionally one or more substances selected from the group consisting of sulfuric acid and salts thereof, hydrochloric acid and salts thereof, organochloro compounds, nitric acid and salts thereof and metals or (ii) cellulose-containing biomass, water, methanesulfonic acid and optionally one or more substances selected from the group consisting of sulfuric acid and salts thereof, hydrochloric acid and salts thereof, organochloro compounds, nitric acid and salts thereof and metals, wherein in each case the total amount of substances selected from the group consisting of sulfuric acid and salts thereof, hydrochloric acid and salts thereof, organochloro compounds, nitric acid and salts thereof and metals in the treatment mixture is not more than 1 wt.-% based on the weight of the methanesulfonic acid present in the treatment mixture.

According to alternative (i) of the method of the present invention, the treatment mixture preferably comprises one or more compounds of formula (I) as defined above (i.e. surfactants of formula (I) as well as compounds of formula (I) which are not surfactants). Within the compounds of formula (I) the groups

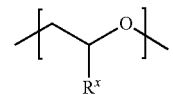

wherein in each case $R^x$ is independently of each further $R^x$ selected from the group consisting of hydrogen and alkyl with 1 to 20 carbon atoms ($C_1$- to $C_{20}$-alkyl) are distributed either in a random manner, gradient manner or block-like.

Compounds of formula (I) with block-like distribution of the groups

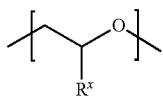

are obtainable by block polymerization.

Compounds of formula (I) with random distribution of the groups

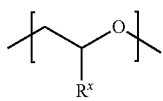

are obtainable when the corresponding monomers are supplied simultaneously to the polymerization reactor.

When $R^1$ and/or $R^2$ are aryl, it is preferred that said aryl is phenyl.

Preferably the one or at least one compound of formula (I) is selected from the group consisting of compounds of formula (I') wherein

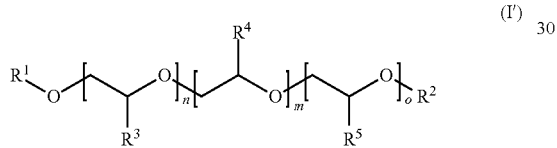

$R^1$ and $R^2$ are as defined for formula (I)
$R^3$ and $R^4$ are independently selected from the group consisting of hydrogen and alkyl with 1 to 3 carbon atoms ($C_1$- to $C_3$-alkyl)
$R^5$ is selected from the group consisting of hydrogen and alkyl with 1 to 20 carbon atoms ($C_1$- to $C_{20}$-alkyl)
wherein preferably $R^4$ is not identical to $R^3$ and $R^4$ is not identical to $R^5$
n, m, o independently of each other are integers from 0 to 800 with the proviso that the sum of m, n and o is 1 or more.

As far as hereinabove or hereinbelow reference is made to the compounds of formula (I) this shall include the compounds of formula (I') which form a subgroup of compounds of formula (I).

In a preferred group of compounds of formula (I), each $R^x$ is hydrogen, x is an integer in the range of from 1 to 800, preferably from 3 to 500, further preferably from 5 to 230 and most preferably from 6 to 140. In said first preferred group of compounds of formula (I) polyethylene glycols are particularly preferred, i.e. $R^1$, $R^2$ and each $R^x$ is hydrogen, x is an integer in the range of from 1 to 800, preferably from 3 to 500, further preferably from 5 to 230 and most preferably from 6 to 140. Suitable compounds of formula (I) of this preferred group are available under the trade name Pluriol® from BASF SE. Within said first preferred group of compounds of formula (I) especially preferred are those wherein $R^1$, $R^2$ and each $R^x$ is hydrogen and x is an integer in the range of from
5 to 10, preferably 6 or 7
or 20 to 25 preferably 22 or 23
or 130 to 140, preferably 135 to 137.

In a preferred group of compounds of formula (I'), $R^3$ and $R^5$ are hydrogen and $R^4$ is selected from the group consisting of alkyls with 1 to 3 carbon atoms ($C_1$- to $C_3$-alkyls), m is an integer in the range of from 1 to 100, preferably 5 to 80, more preferably 15 to 70 and the sum of n and o (n+o) is an integer in the range of from 2 to 250, preferably 4 to 200 wherein preferably n and o are identical. In said preferred group of compounds of formula (I'), copolymers of ethylene oxide and propylene oxide are particularly preferred, wherein $R^1$, $R^2$, $R^3$ and $R^5$ are hydrogen and $R^4$ is methyl, m is an integer in the range of from 15 to 100, preferably 20 to 80, and n and o each are integers in the range of from 1 to 100, preferably 2 to 98, wherein preferably n and o are identical (have the same value). Suitable compounds of formula (I') of this preferred group are available under the trade name Pluronic® from BASF. Within said preferred group of compounds of formula (I') especially preferred are those wherein $R^1$, $R^2$, $R^3$ and $R^5$ are hydrogen and $R^4$ is methyl, m is an integer in the range of from 65 to 75, preferably 69 and n and o are integers in the range of from 90 to 100, wherein preferably n+o (sum of n and o) is 190 to 200, preferably 195, m is an integer in the range of from 25 to 35, preferably 30, and n and o are integers in the range of from 68 to 73, preferably 71, wherein preferably n+o (sum of n and o) is 140 to 145, m is an integer in the range of from 25 to 35, preferably 30, and n and o are integers in the range of from 10 to 15, preferably 13, wherein preferably n+o (sum of n and o) is 20 to 30, preferably 26, m is an integer in the range of from 25 to 35, preferably 30, and n and o are integers in the range of from 2 to 4 wherein preferably n+o (sum of n and o) is 4 to 8, preferably 5 to 6, wherein in each case preferably n and o are identical.

In the method of the present invention, surfactants which are not compounds of formula (I) may be used instead of or in combination with compounds of formula (I) as defined above (i.e. surfactants of formula (I) as well as compounds of formula (I) which are not surfactants). Preferably these surfactants which are not compounds of formula (I) are selected from the group consisting of polyoxyethylene(20) sorbitan monolaurate (available under the trade name "Tween 20"), polyoxyethylene(40) sorbitan monolaurate (available under the trade name "Tween 40")

polyoxyethylene(60) sorbitan monolaurate (available under the trade name "Tween 60)

polyoxyethylene(65) sorbitan monolaurate (available under the trade name "Tween 65")

polyoxyethylene(80) sorbitan monolaurate (available under the trade name "Tween 80"), alkylpolyglucosides wherein the alkyl groups are selected from the group consisting of $C_4$ to $C_{22}$ alkyl, and the number of glucoside units is 1 to 3, anionic derivatives of said alkylpolyglucosides (derivatives of alkylpolyglucosides wherein the glucosidic hydroxy group is substituted by a group which after dissociation carries a negative charge, e.g. by a carboxylate group or a sulfonate group)

fatty alcohols and anionic derivatives of fatty alcohols (derivatives of fatty alcohols wherein the hydroxy group is substituted by a group which after dissociation carries a negative charge) which are not compounds of formula (I), e.g. fatty alcohol sulfates, fatty alcohol ether sulphates, fatty alcohol sulfonates, fatty alcohol phosphates, fatty alcohol ether phosphates, soaps and fatty alcohol ether carboxlyates and salts of said anionic derivatives of fatty alcohols, wherein in said salts the cation is preferably selected from the group consisting of ammonium, alkali metal cations and alkaline earth metal cations.

phosphoric acid diesters of formula (II)

(II)

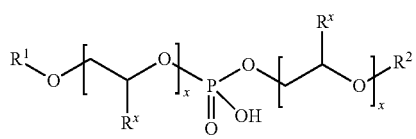

wherein in formula (II)

$R^1$ and $R^2$ are independently selected from the group consisting of hydrogen, unsubstituted and substituted alkyl with 1 to 22 carbon atoms ($C_1$- to $C_{22}$-alkyl) and unsubstituted and substituted aryl, wherein in said substituted $C_1$- to $C_{22}$-alkyl and said substituted aryl each substituent is independently selected from the group consisting of —$OSO_3H$, —$SO_3H$, —COOH and —$OPO_3H_2$ and salts thereof each $R^x$ in said x groups

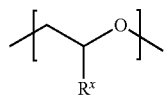

is independently of each further $R^x$ selected from the group consisting of hydrogen and alkyl with 1 to 20 carbon atoms ($C_1$- to $C_{20}$-alkyl)

x is an integer from 1 to 2400.

Without wishing to be bound to any specific theory, it is presently assumed that the compounds selected from the group consisting of compounds of formula (I) and surfactants which are not compounds of formula (I) bind to lignin constituents of the cellulose-containing biomass thus preventing lignin from inhibiting the activity of the enzymes in enzymatic saccharification of the treated cellulose-containing biomass. Furthermore the compounds selected from the group consisting of compounds of formula (I) and surfactants which are not compounds of formula (I) may facilitate swelling of the cellulose-containing biomass, resulting in stabilization of an open structure of the cellulose-containing biomass which improves the access of methanesulfonic acid as well as of enzymes for subsequent enzymatic saccharification. More specifically the molecules of the compounds selected from the group consisting of compounds of formula (I) and surfactants which are not compounds of formula (I) may fill voids in the treated biomass which are formed due to decomposition of hemicellulose and/or lignin, thus avoiding densification and collapsing of the treated cellulose-containing biomass so that in the enzymatic saccharification access of enzymes is facilitated.

Preferably the treatment mixture used in the method according to the invention is obtained by adding an aqueous treatment solution containing either
(i) methanesulfonic acid and one or more compounds selected from the group consisting of compounds of formula (I) and surfactants which are not compounds of formula (I)

or
(ii) methanesulfonic acid and no compound selected from the group consisting of compounds of formula (I) and no surfactant which is not a compound of formula (I)

to said cellulose-containing biomass.

Preferably, in alternative (i) of the above-defined preferred method of the present invention, the aqueous treatment solution contains methanesulfonic acid and one or more compounds of formula (I)

or consists of water, methanesulfonic acid, one or more compounds selected from the group consisting of compounds of formula (I) and surfactants which are not compounds of formula (I), and optionally one or more substances selected from the group consisting of sulfuric acid and salts thereof, hydrochloric acid and salts thereof, organochloro compounds, nitric acid and salts thereof and metals, wherein the total amount of substances selected from the group consisting of sulfuric acid and salts thereof, hydrochloric acid and salts thereof, organochloro compounds, nitric acid and salts thereof and metals in the treatment mixture is not more than 1 wt.-% based on the weight of the methanesulfonic acid present in the aqueous treatment solution.

Most preferably the aqueous treatment solution consists of water, methanesulfonic acid, one or more compounds of formula (I), and optionally one or more substances selected from the group consisting of sulfuric acid and salts thereof, hydrochloric acid and salts thereof, organochloro compounds, nitric acid and salts thereof and metals, wherein the total amount of substances selected from the group consisting of sulfuric acid and salts thereof, hydrochloric acid and salts thereof, organochloro compounds, nitric acid and salts thereof and metals in the treatment mixture is not more than 1 wt.-% based on the weight of the methanesulfonic acid present in the aqueous treatment solution.

According to alternative (ii) of the above-defined preferred method of the present invention, the aqueous treatment solution is free of compounds of formula (I) (surfactants or not)

surfactants which are not compounds of formula (I).

In alternative (ii) of the above-defined preferred method of the present invention, the aqueous treatment solution preferably consists of water, methanesulfonic acid and optionally one or more substances selected from the group consisting of sulfuric acid and salts thereof, hydrochloric acid and salts thereof, organochloro compounds, nitric acid and salts thereof and metals, wherein the total amount of substances selected from the group consisting of sulfuric acid and salts thereof, hydrochloric acid and salts thereof, organochloro compounds, nitric acid and salts thereof and metals in the aqueous treatment solution is not more than 1 wt.-% based on the weight of the methanesulfonic acid present in the aqueous treatment solution.

Preferably the above defined aqueous treatment solution is added to the cellulose-containing biomass in such amount that a treatment mixture is obtained comprising 3 wt. % to 75 wt.-%, more preferably 8 wt.-% to 70 wt.-%, further preferably 15 wt.-% to 60 wt. %, most preferably 25 wt.-% to 50 wt.-%, particularly preferably 30 wt.-% to 45 wt.-% of cellulose containing biomass, in each case based on the total weight of said treatment mixture.

Preferably, the concentration of methanesulfonic acid in said aqueous treatment solution—irrespective of the presence of compounds selected from the group consisting of compounds of formula (I) (surfactants or not) and surfactants which are not compounds of formula (I)—is in the range of from 0.1 wt.-% to 5.5 wt.-%, preferably 0.3 wt.-% to 5.0 wt. %, more preferably 0.7 wt.-% to 3.0 wt.-%, most preferably 1.0 wt.-% to 2.0 wt.-% of methanesulfonic acid, in each case based on the total weight of said aqueous treatment solution.

At a concentration below 0.1 wt.-% based on the total weight of said aqueous treatment solution, the amount of methanesulfonic acid in the treatment mixture is generally too low so that the methanesulfonic acid has no significant effect on the yield of glucose in subsequent saccharification, compared to treated cellulose-containing biomass obtained by processing under identical conditions with the sole exception that the treatment mixture does not comprise methanesulfonic acid. On the other hand, the higher the concentration of methanesulfonic acid in the treatment mixture, the higher is the amount of undesirable by-products resulting from decomposition of cellulose and/or hemicellulose, like furanes, furfural and hydroxymethyl furfural. Formation of these by-products reduces the amount of cellulose available for saccharification and/or inhibits for example the activity of the enzymes needed for the enzymatic saccharification. For this reason, it is preferred that the concentration of methanesulfonic acid does not exceed 5.5 wt.-% based on the total weight of said aqueous treatment solution, and is preferably kept as low as possible. This becomes even more important at higher processing temperatures, because higher processing temperatures also promote the formation of undesired by-products. Thus, the higher the processing temperature, the lower the concentration of methanesulfonic acid should be selected.

Preferably, the concentration of methanesulfonic acid in in the treatment mixture is in the range of from 0.5 wt.-% to 25 wt.-%, more preferably 1 wt.-% to 15 wt.-%, most preferably 2 wt.-% to 10 wt.-% in each case based on the total weight of the cellulose-containing biomass present in the treatment mixture.

In this regard, it should be considered that other acids, e.g. sulfuric acid or nitric acid, if present in the treatment mixture, further promote the formation of undesired by-products. Accordingly, the concentration of such acids is preferably kept low as explained above.

A low concentration of acids is also preferable with respect to subsequent enzymatic saccharification, because the enzyme activity decreases if the pH is too low. Accordingly, a low concentration of acids in the treatment mixture allows direct subjection of the treatment mixture containing the treated cellulose-containing biomass to enzymatic saccharification without removal of the aqueous acid-containing phase (see also below).

Preferably in alternative (i) of the method of the present invention the total concentration of compounds selected from the group consisting of compounds of formula (I) (surfactants or not) and surfactants which are not compounds of formula (I) is 0.01 wt.-% to 5 wt.-%, preferably 0.05 wt.-% to 3.0 wt.-%, more preferably 0.1 wt.-% to 2.0 wt.-%, most preferably 0.1 wt.-% to 1.0 wt.-% in each case based on the total weight of said aqueous treatment solution. Further preferably in alternative (i) of the method of the present invention the total concentration of compounds selected from the group consisting of compounds of formula (I) is 0.01 wt.-% to 5 wt.-%, preferably 0.05 wt.-% to 3.0 wt.-%, more preferably 0.1 wt.-% to 2.0 wt.-%, most preferably 0.1 wt.-% to 1.0 wt.-% and the total concentration of surfactants which are not compounds of formula (I) is 0 wt.-%, in each case based on the total weight of said aqueous treatment solution.

For ionic compounds of formula (I) and ionic surfactants which are not compounds of formula (I), the above-defined concentrations are calculated in each case on the basis of the protonated form.

At a concentration below 0.10 wt.-% based on the total weight of said aqueous treatment solution, the amount of compounds selected from the group consisting of compounds of formula (I) and surfactants which are not compounds of formula (I) in the treatment mixture is too low so that said compounds have no significant effect on the yield of glucose in subsequent saccharification, compared to treated cellulose-containing biomass obtained by processing under identical conditions with the sole exception that the treatment mixture does not comprise any compound selected from the group consisting of compounds of formula (I) and surfactants which are not compounds of formula (I). For economical reasons, the concentration of compounds selected from the group consisting of compounds of formula (I) and surfactants which are not compounds of formula (I) is preferably not more than 5 wt.-% based on the total weight of said aqueous treatment solution. Furthermore, at a concentration of more than 5 wt.-% of surfactants based on the total weight of said aqueous treatment solution, foam may be formed in the treatment mixture, which is detrimental for processing the treatment mixture.

In alternative (ii) of the method of the present invention the total concentration of compounds selected from the group consisting of compounds of formula (I) and surfactants which are not compounds of formula (I) in said aqueous treatment solution is 0 wt.-%.

Especially preferred is a method of the invention wherein two or more, preferably all of the above-described preferred features regarding the composition of the treatment mixture are combined.

Processing Conditions

In the method of the present invention said treatment mixture is subjected to a temperature in the range of form 100° C. to 200° C., preferably of from 110° C. to 180° C., most preferably 120° C. to 175° C. at a pressure in the range of from 1 to 20 bars (100 to 2000 kPa), preferably 1 to 16 bars (100 kPa to 1600 kPa), further preferably in a range of from 1 to 13 (100 to 1300 kPa) bars, most preferably 1 to 10 bars (100 to 1000 kPa) wherein the pressure is selected so that at least a part of the water is in the liquid state.

When the temperature is below 100° C., the yield of glucose obtainable by saccharification of said treated cellulose-containing biomass is significantly reduced. When the temperature is above 200° C., the amount of undesirable by-products resulting from decomposition of cellulose and/or hemicellulose, like furanes, furfural and hydroxymethyl furfural, is too high. Formation of these by-products reduces the amount of cellulose available for saccharification and/or inhibits for example the activity of the enzymes needed for the enzymatic saccharification.

Regarding the selection of the pressure, it is important that the pressure is sufficiently high to avoid complete vaporization of the water, so as to allow interaction between the cellulose-containing biomass and the methanesulfonic acid dissolved in water. On the other hand, for economical and technical reasons the pressure is preferably as low as possible.

Preferably, in the method according to the present invention a temperature in the range of from 100° C. to 200° C. at a pressure in the range of from 1 to 20 bars (wherein the pressure is selected so that at least a part of the water is in the liquid state) is maintained for a duration of not less than 1 minute and not more than 120 minutes, preferably of not less than 1 minute and not more than 60 minutes, further preferably of not less than 1 minute and not more than 30 minutes, particularly preferably of not less than 1 minute and not more than 20 minutes and most preferably of not less than 1 minute and not more than 10 minutes. Thereafter the treatment mixture is allowed to cool and/or the pressure is lowered.

The skilled person is aware of the interdependence between the parameters concentration of methanesulfonic acid, temperature and duration of treatment. Thus, the lower the concentration of methanesulfonic acid the higher the temperature and/or the duration of the treatment have to be selected and vice versa (see also above). Based on his knowledge, the skilled person will select the parameters accordingly, or determine the suitable combination of said parameters by simple routine experimentation.

Especially preferred is a method of the invention wherein two or more, preferably all of the above-described preferred features regarding the processing conditions are combined.

Further preferred is a method of the invention wherein two or more, preferably all of the above-described preferred features regarding the processing conditions and the composition of the treatment mixture are combined.

In this regard especially preferred is a method according to the present invention comprising the steps of
  preparing an aqueous treatment solution containing 0.1 wt.-% to 2.0 wt.-% of methanesulfonic acid and 0.01 wt.-% to 1 wt.-% of one or more compounds of formula (I)
  adding said aqueous treatment solution to said cellulose-containing biomass so that a treatment mixture comprising said cellulose-containing biomass, water and methanesulfonic acid and one or more compounds of formula (I) is obtained, said treatment mixture comprising 30 wt.-% to 45 wt.-% of cellulose containing biomass, based on the total weight of said treatment mixture
  subjecting said treatment mixture to a temperature in the range of from 120° C. to 175° C., wherein said temperature is maintained for a duration of not less than 1 minute and not more than 40 minutes to generate a treated cellulose-containing biomass.

In the above-defined method, the one or more compounds of formula (I) are preferably selected among the above-defined preferred compounds of formula (I).

Processing Equipment

In order to allow for an efficient processing of cellulose-containing biomass according to the present invention, it is important that the solid constituents of the reaction mixture are in intimate contact with the liquid phase of the reaction mixture and—if present—steam formed by partial vaporization of the water of the mixture. This intimate contact preferably exists all the time the reaction mixture is subjected to a temperature in the range of from 100° C. to 200° C. at a pressure in the range of from 1 to 20 bar (wherein the pressure is selected so that at least a part of the water is in the liquid state). Accordingly, for the method of the present invention, any type of reactor may be used which allows meeting this condition.

More specifically a rotating reactor, e.g. in the form of a rotating drum may be used. Alternatively, a reactor having means for mixing the reactants may be used, e.g. a stirred tank reactor. Different mixing means are applicable e.g. pug mixer, paddle mixer, ribbon mixer.

Another suitable type of reactor is a percolation reactor wherein the cellulose-containing biomass is maintained in a fixed bed, e.g. a column, a tube, a drum or a vessel, and the aqueous treatment solution comprising methanesulfonic acid and—if present—one or more compounds selected from the group consisting of compounds of formula (I) and surfactants which are not compounds of formula (I) is flowed through the bed, e.g. a trickle-bed reactor type which allows for liquid flow involving relatively small volume of liquid. Preferably, the reactor is designed so as to allow for recirculation of the aqueous treatment solution comprising methanesulfonic acid and—if present—one or more compounds selected from the group consisting of compounds of formula (I) and surfactants which are not compounds of formula (I).

A further suitable type of reactor is a screw-type reactor. In such type of reactor, radial mixing of solids (i.e. the cellulose-containing biomass) is provided along the length of the reactor shaft, and the aqueous treatment solution comprising methanesulfonic acid and—if present—one or more compounds selected from the group consisting of compounds of formula (I) and surfactants which are not compounds of formula (I) is either in co-current or in counter-current flow to the solids. If present, steam formed by partial vaporization of the water of the aqueous treatment solution is a further constituent of said co-current or counter-current flow to the solids.

Combinations of above mentioned reactor types are possible, too.

The method may be operated in a discontinuous, semi-continuous or continuous operation mode.

Heating of the treatment mixture to the desired processing temperature is achieved by means of electric heating, steam or other suitable means known to those skilled in the art.

The reactor may be designed as a single step reactor so that for further processing steps like saccharification the treated cellulose-containing biomass is removed from the reactor and transferred to one or more further reactors wherein such further processing steps are carried out. Alternatively, the reactor may be designed as a multi-step reactor allowing for subsequent saccharification of the treated cellulose-containing biomass without taking the treated cellulose-containing biomass out of the reactor.

Further Processing Steps

Preferably, the method according to the present invention further comprises a step selected from the group consisting of
  saccharification of the treated cellulose-containing biomass so that glucose and/or other sugars are formed and optionally fermentation and/or chemical processing of the formed glucose and/or other sugars,
  further processing of the treated cellulose-containing biomass to obtain dissolving pulp.

In a first preferred alternative, saccharification of the treated cellulose-containing biomass is effected by means of enzymes (enzymatic saccharification, sometimes also referred to as enzymatic hydrolysis step). In the step of enzymatic saccharification suitable enzymes are added to the treated cellulose-containing biomass to convert the contained cellulose to glucose and/or other sugars, e.g. xylose. Suitable reactors, processing conditions and enzymes for the enzymatic saccharification are known to those skilled in the art. The enzymatic saccharification step is generally performed in stirred-tank reactors or fermentors under controlled pH, temperature, and mixing conditions. The enzymatic saccharification step may last up to 200 hours. Enzymatic saccharification is usually carried out at temperatures from about 30° C. to about 65° C., in particular around 50° C., and at a pH in the range of from about 4 and about 6, especially around pH 5.5. To produce glucose that can be metabolized by yeast, the enzymatic saccharification is typically performed in the presence of a beta-glucosidase enzyme. Preferably an enzyme formulation comprising one or more enzymes selected from the group consisting of beta-glucosidases, exo-cellobiohydrolases, endo- and exo-glucanases, glucoside hydrolases and xylanases is used. In some cases it is preferably to use enzymes which are thermally stable and allow to the enzymatic saccharification to be carried out at temperatures from about 60° C. to about 80° C.

In a second preferred alternative, saccharification is achieved by chemical, especially thermochemical, processing of the treated cellulose-containing biomass, said chemical processing not involving enzymes. More specifically, from the treated cellulose-containing biomass obtainable by the method of the present invention fermentable sugars and lignin can be produced by means of treatment with a supercritical or near-supercritical fluid or by hydrothermal treatment.

The sugars obtained by saccharification of the treated cellulose-containing biomass may serve as feedstock for obtaining a plurality of further products, either by fermentation or by chemical processing of the sugars obtained by saccharification of the treated cellulose-containing biomass.

In the fermentation step, glucose obtained by saccharification of the treated cellulose-containing biomass, is fermented to ethanol by a fermenting organism, such as yeast. Suitable reactors, processing conditions and fermenting organisms for the fermentation are known to those skilled in the art. The steps of enzymatic saccharification and of fermentation are performed simultaneously in one vessel or in separate vessels. In the first alternative, the fermentation is carried out simultaneously with the enzymatic saccharification in the same vessel under controlled pH, temperature, and mixing conditions. Typical products of the fermentation of glucose include ethanol, butanol and succinic acid.

Chemical processing of sugars obtained by saccharification of the treated cellulose-containing biomass refers to processes wherein said sugars are subjected to a chemical reaction not involving fermentation to obtain other chemical products. Preferably, said chemical reaction is carried out in the presence of one or more catalysts which are not enzymes. Typical products obtainable by chemical processing of glucose include sugar alcohols, sugar acids, hydroxymethylfurfural and derivatives thereof.

In a preferred method of the present invention, the liquid phase of the treatment mixture is at least partially separated from the treated cellulose-containing biomass prior to saccharification of the treated cellulose-containing biomass, e.g. by filtration and subsequent washing of the treated cellulose-containing biomass. The liquid phase of the treatment mixture consists of an aqueous solution, which contains hemicellulosic sugars (e.g. xylose) and further water-soluble decomposition products formed in the step of subjecting the treatment mixture to a temperature in the range of from 100° C. to 200° C. at a pressure in the range of from 1 to 20 bars (100 to 2000 kPa). This aqueous solution may be used as a feedstock for further processes. Typical products obtainable by chemical processing of xylose include sugar alcohols, sugar acids, furfural and derivatives thereof.

Separating the liquid constituents of the treatment mixture from the treated cellulose-containing biomass prior to enzymatic separation has the advantage that water-soluble by-products like furanes, furfural and hydroxymethylfurfural which may act as enzyme inhibitors are removed from the treated cellulose-containing biomass which is subjected to enzymatic separation. A disadvantage of this specific method is that compounds selected from the group consisting of compounds of formula (I) (surfactants or not) and surfactants which are not compounds of formula (I) may be removed from the treated cellulose-containing biomass so that the above-described positive effects of the presence of compounds selected from the group consisting of compounds of formula (I) and surfactants which are not compounds of formula (I) during enzymatic saccharification may be reduced.

In an alternative preferred method according to the present invention the enzymes for the saccharification are added to the treatment mixture comprising the treated cellulose-containing biomass without prior removal of the liquid phase from the treated cellulose-containing biomass, thus reducing complexity of the overall processing method. Furthermore, in this method the compounds selected from the group consisting of compounds of formula (I) (surfactants or not) and surfactants which are not compounds of formula (I) remain in the treated cellulose-containing biomass so that the above-described positive effects may be obtained as much as possible. For this specific method of the present invention, it is especially important that the acid concentration in the treatment mixture is low and that the step of subjecting the treatment mixture to a temperature in the range of from 100° C. to 200° C. at a pressure in the range of from 1 to 20 bars (100 to 2000 kPa) is carried out in such manner that the amount of by-products like furanes, furfural and hydroxymethylfurfural which may act as enzyme inhibitors is as small as possible. If necessary the acid in the treatment mixture is neutralized to adjust the pH to a value suitable for enzymatic saccharification.

In a preferred method of the present invention, the composition of the treatment mixture and the temperature and pressure to which said treatment mixture is subjected and the conditions of the saccharification of the treated cellulose-containing biomass so that glucose is formed are selected such that a higher yield of glucose is formed in comparison to a processing wherein all conditions and compositions are identical with the exception that in the treatment mixture methanesulfonic acid is replaced by the same weight of sulfuric acid.

When replacement of methanesulfonic acid in the treatment mixture by the same weight of sulfuric acid under otherwise identical processing conditions (as defined above) results in a lower yield of glucose in a subsequent saccharification of said treated cellulose-containing biomass, this is certainly the result of a different structure and/or constitution of the treated cellulose-containing biomass. Obviously, processing with a treatment mixture comprising methanesulfonic acid instead of sulfuric acid preferably results in a treated cellulose-containing biomass having a structure which facilitates saccharification. Without wishing to be bound to any specific theory, it is presently assumed that processing according to the present invention in preferred cases results in a treated cellulose-containing biomass having a more open and accessible structure and a higher activity towards saccharification.

Another field of application of the present invention is related to the production of dissolving pulp. Dissolving pulp (also called dissolving cellulose) is a bleached wood pulp or cotton linters having a high content of cellulose (>90%). It has a high level of brightness and uniform molecular-weight distribution. This pulp is manufactured for uses that require a high chemical purity, and particularly low hemicellulose content, since the hemicellulose can interfere with subsequent processes. Dissolving pulp is so named because it is not made into paper, but dissolved either in a solvent or by derivatization into a homogeneous solution, which makes it completely chemically accessible and removes any remaining fibrous structure. Once dissolved, it can be spun into textile fibers, or chemically reacted to produce derivatized celluloses, such cellulose triacetate, a plastic-like material formed into fibers or films, or cellulose ethers such as methyl cellulose, used as a thickener. Dissolving pulp is mainly produced chemically from the pulpwood by the sulfite process or the kraft process with an acid prehydrolysis step to at remove hemicelluloses. As noted above, in the treated cellulose-containing biomass obtainable by the method of the present invention the content of hemicellulose and/or lignin is typically decreased due to decomposition to xylose. Therefore, the treated cellulose-containing biomass obtainable by the method of the present invention is suitable for further processing to obtain dissolving pulp.

EXAMPLES

1. Pretreatment of Cellulose-Containing Biomass at 120° C.

An autoclave with baffles and a stirrer is filled with a treatment mixture comprising 4 g chopped straw, 100 g of an aqueous treatment solution containing
  deionized water,
  an acid as specified in type and concentration according to table 1 and 2,
  optionally one or more compounds selected from the group consisting of compounds of formula (I) and surfactants which are not compounds of formula (I), as specified in type and concentration according to table 1 and 2. Hereinbelow and in tables 1 and 2, the compounds selected from the group consisting of compounds of formula (I) and surfactants which are not compounds of formula (I) are commonly referred to as additives. For the chemical structure of said additives, see table 5 hereinbelow.

For preparing the above-defined aqueous treatment solution, sulfuric acid was used in the form of an aqueous solution comprising 96 wt.-% sulfuric acid, and methanesulfonic acid was used in the anhydrous form (>99.5 wt.-% methanesulfonic acid).

The autoclave is purged three times with nitrogen gas and the treatment mixture is heated to 120° C. at a pressure of 1.6 bar (160 kPa) under stirring (800 rpm). After 30 minutes, the heating is turned off, the mixture is allowed to cool to ambient temperature, the autoclave is relaxed and is emptied. The content of the autoclave is transferred to a container. The autoclave is rinsed with approximately 50 mL of deionized water and the resultant aqueous mixture is filled into the container too. The obtained mixture comprising treated cellulose-containing biomass is removed from the container and filtered through a frit (pore size 2), and the weight of the liquid phase obtained as filtrate is determined, see table 1 and 2. The treated cellulose-containing biomass obtained as filtration residue is dried overnight in air, and its weight is determined, see table 1 and 2, and then it is subjected to enzymatic saccharification as described herein below.

2. Enzymatic Saccharification of Cellulose-Containing Biomass Treated at 120° C.

1.25 g of the treated cellulose-containing biomass obtained according to tables 1 and 2 are weighed into a 50 mL tube and are treated with deionized water containing 0.1 wt.-% sodium azide to a volume of 20 mL. A pH-value of 5.5 is adjusted by adding 100 mM phosphate buffer and an enzyme formulation comprising one or more enzymes selected from the group consisting of beta-glucosidases, exo-cellobiohydrolases, endo- and exo-glucanases, glucoside hydrolases and xylanases is added. The mixture is incubated in an Eppendorf-Thermomixer at 300 rpm and 53° C. (50° C. internal). At certain intervals, 1 mL samples were withdrawn and diluted 1:1 with water. After centrifugation the clear supernatant is analyzed by HPLC for the concentrations of glucose and xylose.

3. Pretreatment of Cellulose-Containing Biomass at Temperatures in the Range of from 145° C. to 175° C.

An autoclave with baffles and a stirrer is filled with a treatment mixture comprising 7.5 g chopped straw, 100 g of an aqueous treatment solution containing
  deionized water,
  an acid as specified in type and concentration according to table 3,
  where the acid is methanesulfonic acid, optionally a compound selected from the group consisting of compounds of formula (I) as specified in type and concentration according to table 3 (hereinbelow and in table 3 referred to as an additive. For the chemical structure of said additive, see table 5 hereinbelow.)

For preparing the above-defined aqueous treatment solution, sulfuric acid was used in the form of an aqueous solution comprising 96 wt.-% sulfuric acid, and methanesulfonic acid was used in the anhydrous form (>99.5 wt.-% methanesulfonic acid).

The autoclave is purged three times with nitrogen gas and the treatment mixture is heated to the target temperature according to table 3 at a pressure of max. 9.0 bar (900 kPa) under stirring. After the respective hold time at target temperature according to table 3, the heating is turned off, the mixture is allowed to cool to ambient temperature, the autoclave is relaxed and is emptied. The content of the autoclave is transferred to a container. The obtained mixture comprising treated cellulose-containing biomass is removed from the container and filtered through a frit (pore size 2), and the weight of the liquid phase obtained as filtrate is determined, see table 3. The weight of the treated cellulose-containing biomass obtained as filtration residue is determined, see table 3, and then it is subjected to enzymatic saccharification as described herein below.

4. Enzymatic Saccharification of Cellulose-Containing Biomass Treated at Temperatures in the Range of from 145° C. to 175° C.

4.50 g of the treated cellulose-containing biomass obtained according to table 3 are weighed into a 50 mL tube and are treated with 25.5 g deionized water containing 0.1 wt. % sodium azide. A pH-value of 5.5 is adjusted by adding 100 mM phosphate buffer and an enzyme formulation comprising one or more enzymes selected from the group consisting of beta-glucosidases, exo-cellobiohydrolases, endo- and exo-glucanases, glucoside hydrolases and xylanases is added. The mixture is incubated in an Eppendorf-Thermomixer at 350 rpm and 53° C. (50° C. internal). At certain intervals, 1 mL samples were withdrawn and diluted 1:1 with water. After centrifugation the clear supernatant is analyzed by HPLC for the concentrations of glucose and xylose.

TABLE 1

Generation of treated cellulose-containing biomass in the absence of additives (examples No. 1-3)

| | Example No. | | |
|---|---|---|---|
| | 1 | 2 | 3 |
| Pretreatment of chopped straw to give treated cellulose-containing biomass | | | |
| Mass of chopped straw/g | 4.0 | 4.0 | 4.0 |
| acid type and conc./wt.-% of aqueous treatment solution | / | 1% $H_2SO_4$ | 1% MSA |
| Additive type and conc./wt.-% of aqueous treatment solution | / | / | / |
| Temperature/°C. | 120 | 120 | 120 |
| Time/min | 30 | 30 | 30 |
| Liquid phase/g | 135.8 | 150.2 | 147.1 |
| Treated cellulose-containing biomass/g | 14.8 | 6.6 | 8.1 |
| Enzymatic saccharification | | | |
| Used treated cellulose-containing biomass/g | 1.25 | 1.25 | 1.25 |
| Calculation | | | |
| factor cellulose-containing biomass 'treated/used in saccharification' | 11.84 | 5.28 | 6.48 |
| Yield of glucose from used treated cellulose-containing biomass Glucose/absolute | | | |
| 23 h enzymatic saccharification | 28.65 | 50.05 | 72.06 |
| 96 h enzymatic saccharification | 34.10 | 61.46 | 88.06 |
| Norm: Glucose, 23 h enzymatic saccharification | 28.65 | 28.65 | 28.65 |
| Glucose/normalized absolute | | | |
| 23 h enzymatic saccharification | 1.00 | 1.75 | 2.51 |
| 96 h enzymatic saccharification | 1.19 | 2.14 | 3.07 |

TABLE 2

Generation of treated cellulose-containing biomass in the presence of additives (examples No. 4-11)

| Example No. | 4 | 5 | 6 | 7 | 8 | 9 | 10 | 11 |
|---|---|---|---|---|---|---|---|---|
| Pretreatment of chopped straw to give treated cellulose-containing biomass | | | | | | | | |
| Mass of chopped straw/g | 4.0 | 4.0 | 4.0 | 4.0 | 4.0 | 4.0 | 4.0 | 4.0 |
| Acid type and conc./wt.-% of aqueous treatment solution | / | 1% MSA | 1% MSA | 1% MSA | 1% $H_2SO_4$ | 1% Formic acid | 1% Formic acid | 1% Formic acid |
| Additive type and conc./wt.-% of aqueous treatment solution | / | 2% Pluriol E6000 | 2% Pluronic PE6800 | 2% Tween 20 | 2% Tween 20 | 2% Pluriol E6000 | 2% Pluronic PE6800 | 2% Tween 20 |
| Temperature/°C. | 120° C. | 120° C. | 120° C. | 120° C. | 120° C. | 120° C. | 120° C. | 120° C. |
| Time/min | 30 | 30 | 30 | 30 | 30 | 30 | 30 | 30 |
| Liquid phase/g | 144.4 | 141.7 | 133.9 | 135.9 | 139.0 | 135.7 | 129.3 | 130.8 |
| Treated cellulose-containing biomass/g | 16.6 | 12.8 | 13.6 | 15.1 | 15.1 | 18.8 | 23.0 | 16.5 |
| Enzymatic saccharification | | | | | | | | |
| Used treated cellulose-containing biomass/g | 1.25 | 1.25 | 1.25 | 1.25 | 1.25 | 1.25 | 1.25 | 1.25 |
| Calculation | | | | | | | | |
| factor cellulose-containing biomass 'treated/used in saccharification' | 13.28 | 10.24 | 10.88 | 12.08 | 12.08 | 15.04 | 18.40 | 13.44 |
| Yield of glucose from used treated cellulose-containing biomass Glucose/absolute | | | | | | | | |
| 24 h enzymatic saccharification | 14.42 | 49.34 | 50.17 | 47.12 | 38.67 | 20.97 | 22.17 | 19.71 |
| 48 h enzymatic saccharification | 15.70 | 53.96 | 53.11 | 50.08 | 43.67 | 23.42 | 24.44 | 21.44 |
| Norm: Glucose, 24 h enzymatic saccharification | 14.42 | 14.42 | 14.42 | 14.42 | 14.42 | 14.42 | 14.42 | 14.42 |
| Glucose/normalized absolute | | | | | | | | |
| 24 h enzymatic saccharification | 1.00 | 3.42 | 3.48 | 3.27 | 2.68 | 1.45 | 1.54 | 1.37 |
| 48 h enzymatic saccharification | 1.09 | 3.74 | 3.68 | 3.47 | 3.03 | 1.62 | 1.70 | 1.49 |

TABLE 3

Generation of treated cellulose-containing biomass under varying conditions (examples No. 12-20)

| Example No. | 12 | 13 | 14 | 15 | 16 | 17 | 18 | 19 | 20 |
|---|---|---|---|---|---|---|---|---|---|
| Pretreatment of chopped straw to give treated cellulose-containing biomass | | | | | | | | | |
| Mass of chopped straw/g | 7.5 | 7.5 | 7.5 | 7.5 | 7.5 | 7.5 | 7.5 | 7.5 | 7.5 |
| Acid type and conc./wt.-% of aqueous treatment solution | 0.25% $H_2SO_4$ | 0.25% MSA | 0.25% MSA | 0.10% $H_2SO_4$ | 0.10% MSA | 0.30% $H_2SO_4$ | 0.30% MSA | 0.50% $H_2SO_4$ | 0.50% MSA |
| Additive type and conc./wt.-% of aqueous | / | / | 0.25% | / | / | / | / | / | / |

TABLE 3-continued

Generation of treated cellulose-containing biomass under varying conditions (examples No. 12-20)

| Example No. | 12 | 13 | 14 | 15 | 16 | 17 | 18 | 19 | 20 |
|---|---|---|---|---|---|---|---|---|---|
| treatment solution | | | Pluriol E6000 | | | | | | |
| Temperature/° C. | 165° C. | 165° C. | 165° C. | 175° C. | 175° C. | 160° C. | 160° C. | 145° C. | 145° C. |
| Time/min | 20 | 20 | 20 | 40 | 40 | 20 | 20 | 0 | 0 |
| Liquid phase/g | 120.8 | 125.2 | 114.5 | 121.9 | 126.0 | 119.7 | 121.3 | 117.1 | 117.4 |
| Treated cellulose-containing biomass/g | 21.9 | 18.8 | 28.0 | 22.7 | 16.9 | 18.6 | 22.5 | 27.1 | 27.3 |
| | | | Enzymatic saccharification | | | | | | |
| Used treated cellulose-containing biomass/g | 4.50 | 4.50 | 4.50 | 4.50 | 4.50 | 4.50 | 4.50 | 4.50 | 4.50 |
| | | | Calculation | | | | | | |
| factor cellulose-containing biomass 'treated/used in saccharification' | 4.87 | 4.18 | 6.22 | 3.76 | 5.04 | 4.13 | 5.00 | 6.02 | 6.07 |
| | | Yield of glucose from used treated cellulose-containing biomass | | | | | | | |
| | | | Glucose/absolute | | | | | | |
| 24 h enzymatic saccharification | 39.37 | 49.34 | 89.60 | 45.82 | 60.78 | 40.09 | 58.42 | 39.14 | 56.90 |
| Norm: Glucose, 24 h enzymatic saccharification/example 12 | 39.37 | 39.37 | 39.37 | 39.37 | 39.37 | 39.37 | 39.37 | 39.37 | 39.37 |
| | | | Glucose/normalized absolute | | | | | | |
| 24 h enzymatic saccharification | 1.00 | 1.25 | 2.28 | 1.16 | 1.54 | 1.02 | 1.48 | 0.99 | 1.45 |

TABLE 4

Properties of the acids used

| | Acid | | |
|---|---|---|---|
| | MSA | $H_2SO_4$ | Formic acid |
| $pk_A$ | −1.9 | −3.0 (first pKa) 1.9 (second pKa) | 3.8 |
| Corrosivity* | 3 | 4 | 2 |
| Oxidizing* | 1 | 3 | 1 |
| Reducing* | 1 | 2 | 5 |
| Vapor pressure* | 1 | 1 | 5 |
| Temperature stability | 1 | 1 | 3 |

*1 = excellent 5 = poor

TABLE 5

| Additive name | Compound of formula (I) | Chemical structure |
|---|---|---|
| Pluriol E6000 | yes | polyethylene glycol having an average molecular weight of 6000 g/mol |
| Pluronic PE6800 | yes | block copolymer having a central polypropylene glycol block (molar mass = 1750 g/mol) flanked by two polyethylene glycol blocks wherein the percentage of said polyethylene glycol blocks of the molar mass of the molecule is 80%. |
| Tween 20 | no | polyoxyethylene(20) sorbitan monolaurate |

Tables 1 and 2 show the conditions of the generation of treated cellulose-containing biomass from wheat straw at 120° C. for 30 min, using different acids (sulfuric acid, methanesulfonic acid, formic acid, see table 1) in the absence (table 1) or presence of an additive (see table 2), and show the yields of glucose after the enzymatic saccharification of the treated cellulose-containing biomass.

Table 3 shows the conditions of the generation of treated cellulose-containing biomass from wheat straw at different temperatures in the range of from 145° C. to 175° C. using different acids (sulfuric acid or methanesulfonic acid, see table 3) in the absence (examples 12, 13 and 15-20) or presence of an additive (only for methanesulfonic acid, see example 14), and show the yields of glucose after the enzymatic saccharification of the treated cellulose-containing biomass. Due to the higher treatment temperature, in examples 12-20 the duration of the treatment and the acid concentration in the treatment mixture are reduced, compared to the treatment at 120° C. of examples 1-11.

The "yields" indicated in tables 1, 2 and 3 are either absolute yields stated in arbitrary units or normalized absolute yields. Thus, the yields are not based on a theoretical yield. The yields of glucose obtained after the enzymatic saccharification are extrapolated to the quantity of treated cellulose-containing biomass and normalized in tables 1 and 2 with respect to the reference of example No. 1 or No. 4, respectively (pretreatment with water at 120° C.), and in table 3 with respect to the reference of example No. 12 (pretreatment with sulfuric acid at 165° C.).

Surprisingly, in the absence of any compounds selected from the group consisting of compounds of formula (I) and surfactants which are not compounds of formula (I) the use of methanesulfonic acid as acid in the pretreatment of the present invention described above results in a higher yield of glucose after 23 h and 96 h of enzymatic saccharification compared to the use of the same weight of sulfuric acid in the pretreatment (example No. 2 compared with example No. 3, table 1; example No. 12, 15, 17, 19, resp., compared with example No. 13, 16, 18, 20, resp., in table 3).

A pretreatment using a combination of methanesulfonic acid with a compound of formula (I) (Pluriol E6000 or Pluronic PE6800) or a surfactant which is not a compound of formula (I) (Tween 20) results in an even higher yield of glucose after 24 h and 48 h of subsequent enzymatic saccharification (examples No. 5-6, table 2 in comparison with example 3 in table 1, example No. 14 in comparison with example No. 13, table 3).

In more detail, table 2 shows yields of glucose after 24 and 48 h of enzymatic saccharification of treated cellulose-containing biomass obtained by using combinations of acid (selected from the group consisting of sulfuric acid, methanesulfonic acid, formic acid) and an additive in the pretreatment. In every case, the combination of methanesulfonic acid with either a compound of formula (I) (Pluronic PE6800 or Pluriol E6000) or a surfactant which is not a compound of formula (I) (Tween 20) according to the present invention in the pretreatment results in a much higher yield of glucose than a combination of formic acid with the respective additive, and in a higher yield of glucose than a combination of sulfuric acid with the additive Tween 20 (Example 8).

Table 4 shows the chemical properties of the used acids and attributes a value to selected properties between 1 and 5 (1 for excellent and 5 for poor) based on their practicability in the method described above. The problem of corrosivity of sulfuric acid (value 4) can be solved by replacing it with formic acid (value 2), but the yields are poor in comparison to methanesulfonic acid (examples No. 5-7 vs. examples No. 9-11), and therefore the use of formic acid appears not acceptable. Surprisingly, however, the use of methanesulfonic acid in the pretreatment of the present invention as described above results in similar or higher yields of glucose than the use of sulfuric acid and alleviates the problem of high corrosivity. In addition, methanesulfonic acid provides the advantages of low vapor pressure and excellent temperature stability similar to sulfuric acid, in contrast to formic acid.

It is noted that in the above-described examples the concentration of cellulose-containing biomass based on the total weight of the treatment mixture is rather close to the lower limit of the above-defined preferred range of 3 wt.-% to 75 wt.-%. However it is common practice in the technical field of the present invention that the effect of an additive with respect to biomass is initially studied in the presence of a low concentration of biomass. Based on the results gained from the examples described herein, the skilled person based on his knowledge is capable of routinely scaling up the method of the present invention to higher concentrations of cellulose-containing biomass.

The invention claimed is:

1. Method for processing a cellulose-containing biomass, comprising
    subjecting a treatment mixture comprising 15% wt.-% to 75 wt.-% cellulose containing biomass based on the total weight of said treatment mixture, water, and methanesulfonic acid
    to a temperature in the range of from 100° C. to 200° C. at a pressure in the range of from 1 to 20 bars (100 to 2000 kPa) wherein the pressure is selected so that at least a part of the water is in the liquid state
    to generate a treated cellulose-containing biomass comprising cellulose, hemicellulose and lignin as major components with decreased amounts of hemicellulose and/or lignin,
    (i) wherein said treatment mixture further comprises one or more compounds selected from the group consisting of
    compounds of formula (I)

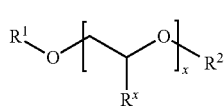

and a surfactant which is not a compound of formula (I), wherein in formula (I) $R^1$ and $R^2$ are independently selected from the group consisting of hydrogen, unsubstituted and substituted alkyl with 1 to 22 carbon atoms ($C_1$- to $C_{22}$-alkyl) and unsubstituted and substituted aryl, wherein in said substituted Cr to C22-alkyl and said substituted aryl each substituent is independently selected from the group consisting of —$OSO_3H$, —$SO_3H$, —COOH and —$OPO_3H_2$ and salts thereof
    each $R^x$ in said x groups
    is independently of each further Rx selected from the group consisting of hydrogen and alkyl with 1 to 20 carbon atoms (Cr to C20-alkyl)
    x is an integer from 1 to 2400
    or
    (ii) wherein said treatment mixture does not comprise any compound selected from the group consisting of compounds of formula (I) as defined above and does not comprise any surfactant which is not a compound of formula (I) as defined above.

2. Method according to claim 1, wherein the one or at least one compound of formula (I) is selected from the group consisting of compounds of formula (I')
    wherein

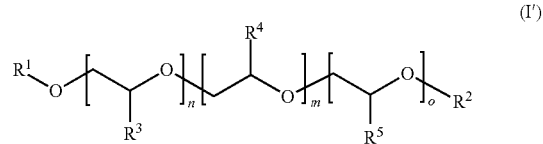

$R^1$ and $R^2$ are as defined for formula (I)
    $R^3$ and $R^4$ are independently selected from the group consisting of hydrogen and alkyl with 1 to 3 carbon atoms ($C_1$- to $C_3$-alkyl)
    $R^5$ is selected from the group consisting of hydrogen and alkyl with 1 to 20 carbon atoms ($C_1$- to $C_{20}$-alkyl)
    wherein preferably $R^4$ is not identical to $R^3$ and $R^4$ is not identical to $R^5$
    n, m, o independently of each other are integers from 0 to 800 with the proviso that the sum of m, n and o is 1 or more.

3. Method according to claim 1, wherein
    said cellulose-containing biomass is selected from the group consisting of plant biomass, agricultural wastes, forestry residues, sugar processing residues, paper waste, and blends thereof.

4. Method according to claim 1, wherein
    the temperature in the range of from 100° C. to 200° C. at a pressure in the range of from 1 to 20 bars (100 kPa to 2000 kPa) wherein the pressure is selected so that at least a part of the water is in the liquid state
    is maintained for a duration of not less than 1 minute and not more than 120 minutes.

5. Method according to claim 1, wherein
    the temperature is in a range of 110° C. to 180° C.

6. Method according to claim 1, wherein
    the pressure is in a range of from 1 to 16 bars (100 kPa to 1600 kPa).

7. Method according to claim 1, wherein
    said treatment mixture comprises 25 wt.-% to 75 wt.-% of cellulose-containing biomass, based on the total weight of said treatment mixture.

8. Method according to claim 1, wherein
    in the treatment mixture the total amount of acids selected from the group consisting of sulfuric acid, nitric acid, hydrochloric acid, and phosphoric acid is 100 wt.-% or less, based on the weight of the methanesulfonic acid present in the treatment mixture.

9. Method according to claim 1, wherein the treatment mixture consists of
(i) cellulose-containing biomass, water, methanesulfonic acid, one or more compounds selected from the group consisting of compounds of formula (I) and surfactants which are not compounds of formula (I), and optionally one or more substances selected from the group consisting of sulfuric acid and salts thereof, hydrochloric acid and salts thereof, organochloro compounds, nitric acid and salts thereof, and metals
or
(ii) cellulose-containing biomass, water, methanesulfonic acid, and optionally one or more substances selected from the group consisting of sulfuric acid and salts thereof, hydrochloric acid and salts thereof, organochloro compounds, nitric acid and salts thereof, and metals
wherein in each case the total amount of substances selected from the group consisting of sulfuric acid and salts thereof, hydrochloric acid and salts thereof, organochloro compounds, nitric acid and salts thereof and metals in the treatment mixture is not more than 1 wt.-% based on the weight of the methanesulfonic acid present in the treatment mixture.

10. Method according to claim 1, wherein
the compound of formula (I) or one, more, or all of the compounds of formula (I) are selected from the group consisting of
compounds of formula (I) wherein $R^1$, $R^2$ and each Rx is hydrogen, x is an integer in the range of from 1 to 800,
and
compounds of formula (I') wherein $R^1$, $R^2$, $R^3$ and $R^5$ are hydrogen and $R^4$ is methyl, m is an integer in the range of from 15 to 100, and n and o each are integers in the range of from 1 to 100.

11. Method according to claim 1, wherein
the treatment mixture is obtained by adding an aqueous treatment solution containing
(i) methanesulfonic acid and one or more compounds selected from the group consisting of compounds of formula (I) and the surfactant which is not a compound of formula (I)
or
(ii) methanesulfonic acid and no compound selected from the group consisting of compounds of formula (I) and no surfactant which is not a compound of formula (I)
to said cellulose-containing biomass.

12. Method according to claim 11, wherein in said aqueous treatment solution
the concentration of methanesulfonic acid is in the range of from 0.1 wt.-% to 5.5 wt.-%,
and
the total concentration of compounds selected from the group consisting of compounds of formula (I) and the surfactant which is not a compound of formula (I) is
(i) in the range of from 0.01 wt.-% to 5 wt.-%,
or
(ii) 0 wt.-%
in each case based on the total weight of said aqueous treatment solution.

13. Method according to claim 1 comprising
preparing an aqueous treatment solution containing 0.1 wt.-% to 2.0 wt.-% of methanesulfonic acid and 0.01 wt.-% to 1 wt.-% of one or more a compound of formula (I)
adding said aqueous treatment solution to said cellulose-containing biomass so that a treatment mixture comprising said cellulose-containing biomass, water and methanesulfonic acid and one or more compound of formula (I) is obtained, said treatment mixture comprising 30 wt.-% to 45 wt.-% of cellulose containing biomass, based on the total weight of said treatment mixture
subjecting said treatment mixture to a temperature in the range of from 120° C. to 175° C., wherein said temperature is maintained for duration of not less than 1 minute and not more than 40 minutes to generate a treated cellulose-containing biomass.

14. Method according to claim 1 further comprising a step selected from the group consisting of
saccharification of the treated cellulose-containing biomass so that glucose and/or other sugars are formed, and optionally fermentation and/or chemical processing of the formed glucose and/or other sugars, and
further processing of the treated cellulose-containing biomass to obtain dissolving pulp.

15. Method according to claim 14, wherein
the composition of the treatment mixture and the temperature and pressure to which said treatment mixture is subjected and the conditions of the saccharification of the treated cellulose-containing biomass so that glucose is formed
are selected such that a higher yield of glucose is formed in comparison to a processing wherein all conditions and compositions are identical with the exception that in the treatment mixture methanesulfonic acid is replaced by the same weight of sulfuric acid.

16. Treated cellulose-containing biomass obtained by the method of claim 1.

* * * * *